United States Patent [19]

Nagpal

[11] Patent Number: 4,492,683

[45] Date of Patent: Jan. 8, 1985

[54] METHOD FOR INHIBITING THE GROWTH OF FUNGI WITH PHENYL GLYCINE COMPOUNDS

[75] Inventor: Krishen L. Nagpal, Williamsville, N.Y.

[73] Assignee: Buffalo Color Corporation, West Paterson, N.J.

[21] Appl. No.: 406,007

[22] Filed: Aug. 6, 1982

[51] Int. Cl.³ .................. A01N 37/10; A01N 37/12
[52] U.S. Cl. ..................... 424/309; 424/319; 560/43; 560/34; 560/22; 560/16; 560/12; 562/457; 562/430; 562/435
[58] Field of Search ........... 560/43, 34; 562/457; 424/309, 319

[56] References Cited

U.S. PATENT DOCUMENTS

| | | | |
|---|---|---|---|
| 2,273,556 | 2/1942 | Bean | 560/43 |
| 2,293,034 | 8/1942 | Moore | 560/43 X |
| 2,296,331 | 9/1942 | Bogemann et al. | 560/43 X |
| 2,374,337 | 4/1943 | Dickey et al. | 560/43 X |
| 3,598,859 | 8/1971 | Yates et al. | |
| 3,994,713 | 11/1976 | Haddock et al. | 560/43 X |
| 4,025,648 | 5/1977 | Hubele | 560/43 X |
| 4,032,657 | 6/1977 | Moser | 560/43 X |

Primary Examiner—Bernard Helfin
Attorney, Agent, or Firm—Michael L. Dunn; Donald C. Studley; Arthur S. Cookfair

[57] ABSTRACT

New compounds and a method for inhibiting the growth of fungus is disclosed which comprises contacting said fungus with a fungicidal amount of a phenyl glycine compound of the formula:

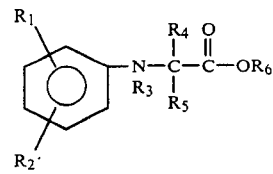

wherein $R_1$ and $R_2$ are independently hydrogen, lower alkyl, substituted lower alkyl, cycloalkyl, substituted cycloalkyl, alkenyl, phenyl, substituted phenyl, halogen, amino or hydroxy groups; $R_3$ is a hydrogen, lower alkyl, substituted lower alkyl, cycloalkyl, benzoyl, halo or nitro substituted benzoyl, substituted cycloalkyl, methylcarbamoyl, cyclohexylcarbamoyl, phenylcarbamoyl, halophenylcarbamoyl, methylphenylcarbamoyl, methylthiocarbamoyl, phenyl, substituted phenyl, napthyl group or —$SO_2R_7$ where $R_7$ is a hydrogen, alkyl, substituted alkyl, phenyl, substituted phenyl or amino group; $R_4$ and $R_5$ are independently hydrogen, lower alkyl or substituted lower alkyl groups and $R_6$ is a hydrogen, lower alkyl or substituted lower alkyl, alkenyl or substituted alkenyl group.

6 Claims, No Drawings

METHOD FOR INHIBITING THE GROWTH OF FUNGI WITH PHENYL GLYCINE COMPOUNDS

TECHNICAL FIELD

This invention relates to new fungicidally active compounds and to a method for inhibiting the growth of fungus by applying to the locus thereof a fungicidal amount of a compound of the formula:

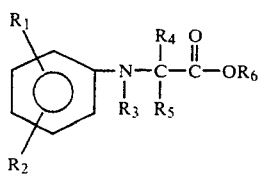

wherein $R_1$ and $R_2$ are independently hydrogen, lower alkyl, substituted lower alkyl, cycloalkyl, substituted cycloalkyl, alkenyl, phenyl, substituted phenyl, halogen, amino or hydroxy groups; $R_3$ is a hydrogen, lower alkyl, substituted lower alkyl, cycloalkyl, benzoyl, halo or nitro substituted benzoyl, substituted cycloalkyl, methylcarbamoyl, cyclohexylcarbamoyl, phenylcarbamoyl, halophenylcarbamoyl, methylphenylcarbamoyl, methylthiocarbamoyl, phenyl, substituted phenyl, naphthyl group or $-SO_2R_7$ where $R_7$ is a hydrogen, alkyl, substituted alkyl, phenyl, substituted phenyl or amino group; $R_4$ and $R_5$ are independently hydrogen, lower alkyl or substituted lower alkyl groups and $R_6$ is a hydrogen, lower alkyl, substituted lower alkyl, alkenyl or substituted alkenyl group; to fungicidal methods employing said phenyl glycine compounds; and to fungicidal compositions containing said phenyl glycine compounds.

BACKGROUND ART

The control of fungi has become of increasing concern to man and has developed a broad need for new products and methods which will exhibit effective fungicidal activity on a variety of microorganisms. In controlling the diseases of agricultural and horticultural crops a particular need has arisen as plant pathogens have emerged which are resistant to heretofore popular commerical fungicides, becoming a serious practical problem in crop protection. The present invention addresses these and other problems by providing new fungicidally active phenyl glycine compounds. The term "fungicide" and "fungicidal amounts" as used herein includes not only chemicals and amounts of chemicals which kill fungi but also that which will inhibit the growth, reproduction or other undesirable effect of fungi.

U.S. Pat. No. 2,654,754 discloses that various aromatic heterocyclic glycine amides have pharmacological activity. U.S. Pat. No. 3,882,162 and its U.S. Pat. No. Re. 29,468, discloses various N-(phenyl)α-amino carboxylic acid esters as having herbicidal activity. U.S. Pat. No. 4,260,782 discloses a method of preparing various alkoxy carbonylethyl dialkylanilines and their use as intermediates for the preparation of compounds having a pesticidal action.

DISCLOSURE OF THE INVENTION

Now, surprisingly, I have found novel phenyl glycine esters, having fungicidal activity, of the formula

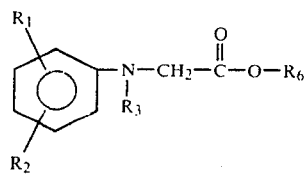

wherein $R_1$ and $R_2$ are independently hydrogen, lower alkyl, substituted lower alkyl, cycloalkyl, substituted cycloalkyl, alkenyl, phenyl, substituted phenyl, halogen, amino or hydroxy groups; $R_3$ is hydrogen, lower alkyl, substituted lower alkyl, cycloalkyl, benzoyl, nitro or halo substituted benzoyl, substituted cycloalkyl, phenyl, substituted phenyl, methylcarbamoyl, cyclohexylcarbamoyl, phenylcarbamoyl, halophenylcarbamoyl, methylphenylcarbamoyl, methylthiocarbamoyl, naphthyl or $-SO_2R_7$ wherein $R_7$ is hydrogen, alkyl, substituted alkyl, phenyl, substituted phenyl or amino; and R is lower alkyl, substituted lower alkyl, alkenyl or substituted alkenyl group; providing when $R_1$ and $R_2$ are lower alkyl and $R_3$ is hydrogen, then $R_6$ is substituted lower alkyl, alkenyl or substituted alkenyl.

Further, I have surprisingly found a method for inhibiting the growth of a fungus which comprises contacting the fungus with a fungicidal amount of a compound of the formula:

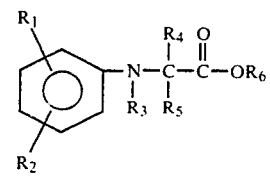

wherein $R_1$ and $R_2$ are independently hydrogen, lower alkyl, substituted lower alkyl, cycloalkyl, substituted cycloalkyl, alkenyl, phenyl, substituted phenyl, halogen, amino or hydroxy groups $R_3$ is a hydrogen, lower alkyl, substituted lower alkyl, cycloalkyl, benzoyl, halo or nitro substituted benzoyl, substituted cycloalkyl, methylcarbamoyl, cyclohexylcarbamoyl, phenylcarbamoyl, halophenylcarbamoyl, methylphenylcarbamoyl, methylthiocarbamoyl, phenyl, substituted phenyl, naphthyl group or $-SO_2R_7$ is a hydrogen, alkyl, substituted alkyl, phenyl, substituted phenyl or amino group; $R_4$ and $R_5$ are independently hydrogen, lower alkyl or substituted lower alkyl groups and $R_6$ is hydrogen, lower alkyl, substituted lower alkyl, alkenyl or substituted alkenyl group.

Representative alkyl groups encompassed within the description of $R_1$, $R_2$, $R_3$, $R_4$, $R_5$, $R_6$ and $R_7$ include substituted and unsubstituted, branched and straight chain methyl, ethyl, propyl, butyl, pentyl and the like up to about 10 carbon atoms. Representative cycloalkyl include substituted and unsubstituted cyclopropane, cyclobutane, cyclopentane and cyclohexane. Representative alkenyl include substituted and unsubstituted ethylene, propylene, 1-butylene, 2-butylene, 1, 2 or 3-pentylene, 1, 2, 3 or 4-hexylene and their geometric isomers and the like up to about 10 carbon atoms. Representative substituents for the alkyl, cycloalkyl and alkenyl groups include halogen, such as chlorine, iodine, fluorine and bromine, hydroxy, nitro and amino. Representative substitutents for the substituted phenyl groups encompassed within the description of $R_1$, $R_2$, $R_3$, $R_4$, $R_5$ and $R_6$ include lower alkyl and alkenyl of 1–3 carbon atoms, hydroxy, chlorine, fluorine or bromine, halogenated lower alkyl and alkenyl of 1–3 carbon atoms nitro and amino. Representative substituents for the substituted urea's encompassed within the description of $R_3$ include substituted and unsubstituted lower alkyl, alkenyl and cycloalkenyl of 1–10 carbon atoms wherein the substituents include hydroxy, halogen, nitro and amine; hydroxy, halogen, particularly chlorine, fluorine and bromine; nitro; substituted and unsubstituted amine, phenyl and naphthyl wherein the substituents include halogen, hydroxy, lower alkyl, lower halo alkyl and lower hydroxy alkyl.

The compounds of the instant invention can generally be prepared by refluxing an appropriate substituted or unsubstituted N-phenyl glycine of the structure:

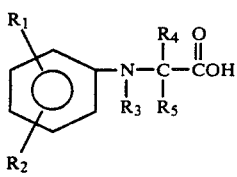

wherein $R_1$, $R_2$, $R_3$, $R_4$ and $R_5$ are as previously described with an appropriate substituted or unsubstituted alkyl or alkenyl alcohol or ester.

A suitable solvent may be used, one which is unreactive in the refluxing procedure, however in most instances the reflux may be accomplished without a solvent. Refluxing conditions are dependent upon the reactants and products but usually require a temperature of from about 50° to about 200° Celsius and a time from about several minutes to two days or more. Refluxing can be done in the presence of a suitable catalyst and I have found that using a concentrated sulfuric acid catalyst is effective. The excess reactant is distilled off and the desired product can be readily attained from the residue by standard extraction techniques.

In instances where $R_3$ of the desired compound is $-SO_2R_7$, the refluxing reactant is an N-phenyl glycinate wherein $R_3$ is hydrogen. After refluxing with a suitable alcohol or ester, the resulting compound is further reacted with an appropriate sulfonyl chloride to produce the desired product by the reaction scheme.

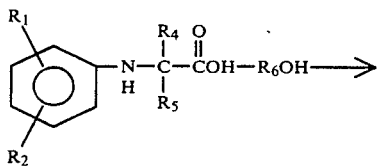

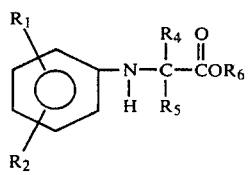

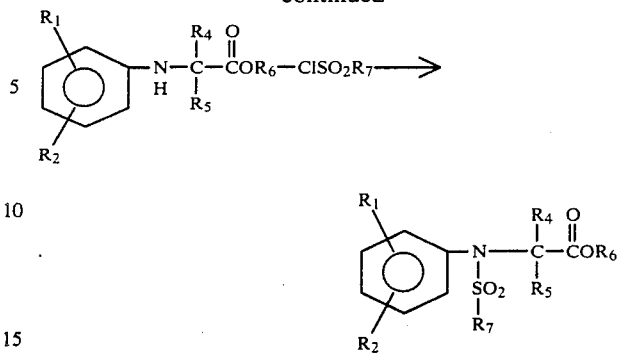

Typical compounds formed by the process of this invention include: methyl-N-phenyl glycinate, ethyl-N-phenyl glycinate, n-propyl-N-phenyl glycinate, n-butyl-N-phenyl glycinate, n-hexyl-N-phenyl glycinate, n-heptyl-N-phenyl glycinate, n-decyl-N-phenyl glycinate, 2-chloroheptyl-N-phenyl glycinate, 2,2-dichloroheptyl-N-phenyl glycinate, 2-hydroxyethyl-N-phenyl glycinate, 2-hydroxypentyl-N-phenyl glycinate, ethenyl-N-phenyl glycinate, propenyl-N-phenyl glycinate, heptenyl-N-phenyl glycinate, chlorobutenyl-N-phenyl glycinate, hydroxybutenyl-N-phenyl glycinate, 2,5-dichloroheptyl-N-2-trifluoromethylphenyl glycinate, propyl-N-phenyl-N-parafluorobenzoyl glycinate, heptenyl-N-4-chlorophenyl glycinate, butyl-N-4-methylphenyl glycinate, decyl-N-3-nitro phenyl glycinate, chloroethyl-N-2-methyl-4-dichloromethylphenyl glycinate, n-hexyl-N-phenyl glycinate, n-propyl-N-phenyl glycinate, isobutyl-N-phenyl glycinate, n-decyl-N-phenyl glycinate, sec. butyl-N-phenyl-N-p-fluorosulfonylbenzoyl glycinate, allyl-N-(p-toluene sulfonyl)-N-phenyl glycinate, methyl-N-(4-chlorobenzene sunfonyl)-N-phenyl glycinate isobutyl-N-(m-chlorophenyl carbamoyl)-N-phenyl glycinate, ethyl-(N-methyl carbamoyl)N-phenyl glycinate, isobutyl-(N-methyl carbamoyl)N-phenyl glycinate and the like.

The novel phenyl glycine compounds of the invention are generally biologically active as fungicides by which is meant that they are generally useful for killing, inhibiting the growth or otherwise inhibiting the undesirable effects of fungi microorganisms. The novel compounds also generally have use in herbicidal, insecticidal and/or nematicidal compositions or as intermediates for the production thereof.

The compounds and method of the invention may be applied directly to the fungi or generally throughout the environment and/or medium of the fungi. They may be applied as solutions, emulsions, suspensions, adducts or the like. The form of application depends upon the purpose to which the fungicide is being directed so as to insure an appropriate distribution thereof. The compounds can be formed into compositions with various conventional inert carriers, e.g. liquid or solid agents normally associated with biologically active compounds, or other active pesticidal compounds to obtain multiple or added biological effect.

Suitable solid carriers include clays, silicates, synthetic hydrated silicon dioxides, resins, waxes, synthetic polymeric materials, carbon, sulfur and the like. Organic materials such as walnut-shell flour, cottonseed hulls, wheat flour, wood flour or redwood-bark flour can also be used as solid carriers.

Suitable liquid carriers include water, alcohols, ketones, aromatic hydrocarbons, aliphatic hydrocarbons, chlorinated aliphatic and aromatic hydrocarbons, petroleum fractions such as kerosene and the like.

In addition to the carrier, the fungicidal composition may contain a surface active agent. Such agents are those commonly known as wetting agents, disbursing agents and emulsifying agents and may be anionic, cationic or nonionic. Examples of suitable surface active agents include alkyl aryl sulfonates, alkyl sulfates containing more than ten carbon atoms, alkylphenol/ethylene oxide condensates, sorbitan esters of fatty acids, alkylamide sulfonates, ethyloxide/fatty acid ester condensates and the like. The biologically active fungicidal composition may also contain other biologically active compounds, adjuvants, stabilizers, conditioners, fillers and the like.

The biologically active fungicidal composition containing an inert carrier, surface active agent or other adjuvant, stabilizer, conditioner, filler or the like may be formulated as a wettable powder, a dust, granule, concentrate, solution, emulsifiable concentrate or the like.

The amount of the biologically active fungicidal compound necessary to kill or inhibit the growth of various fungi will vary with the specific compound utilized, the species it is applied to, the type of formulation and the environmental condition and the like at the time of application and during the period of activity.

Under a particular set of conditions for a particular fungicidal compound, in a particular formulation, the appropriate amount of compound may be readily ascertained.

The biologically active composition may contain from about 0.001 to about 98 percent by weight of the fungicidal compound based upon the total weight of the composition.

Though the compounds of the instant invention display a broad range of fungicidal activity various specific compounds display higher activity to various specific fungi. Generally the compounds of the instant invention have been found very effective on foliage fungi such as bean rust, bean powdery mildew, anthracnose and the like and soil fungi such as pythium, rhizoctonia and the like. It should be understood that though each of the compounds of the instant invention have at least some fungicidal activity, the type and extent of economically desirable activity varies from compound to compound in the selection of moieties represented by the various R groups. In many instances even slight changes in the R groups may result in significant changes in the activity of a compound and the fungi against which it is economically effective.

The following examples are meant to illustrate the invention. Unless otherwise indicated all percentages are in parts by weight and all temperatures in celsius.

EXAMPLE I n-Hexyl-N-Phenyl Glycinate

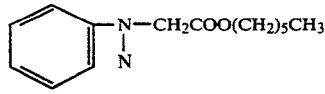

A mixture of N-phenyl glycine (50 g, 0.33 moles), n-hexyl alcohol (400 ml) and concentrated sulfuric acid (4 ml) was refluxed with stirring for 6 hours. The excess hexyl alcohol was removed under vacuum and the residue was poured onto water. The aqueous mixture was extracted with methylene chloride (4 × 100 ml), washed with water and dried over anhydrous MgSO$_4$.

The residue was distilled under reduced pressure to produce 36 g, (0.153 mole) of the above-identified product having a melting point of 44° C.

EXAMPLE II n-Propyl-N-Phenyl Glycinates

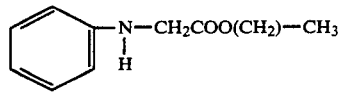

A mixture of phenyl glycine (50 g, 0.33 mole), n-propanol (400 ml) and concentrated sulfuric acid (4 ml) was refluxed with stirring for 6 hours. After cooling, the solution was poured onto ice water, with stirring, and the product collected by filtration. 38 grams of the above-identified product was recovered.

EXAMPLE III

Isobutyl-N-Phenyl Glycinate

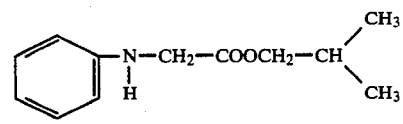

A mixture of phenyl glycine (50 g, 0.33 mole), isobutyl alcohol (400 ml) and concentrated sulfuric acid (4 ml) was refluxed for 6 hours. The excess isobutyl alcohol was removed and the residue was poured onto ice water. The product separated and was collected by filtration producing 48 grams of the above-identified product having a melting point of 54° C.

EXAMPLE IV n-Decyl-N-Phenyl Glycinate

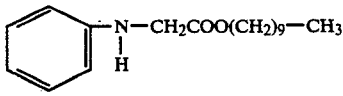

N-phenyl glycine (50 g, 0.33 mole) was refluxed with n-decyl alcohol (400 ml) and concentrated sulfuric acid (4 ml) for 6 hours. The decanol was removed under vacuum and the residue was poured onto ice water with stirring. The crude product that separated out was collected and washed with water. It was crystallized twice from aqueous alcohol and produced 60 grams of the above-identified product having a melting point of 52° C.

EXAMPLE V

Sec. Butyl-N-Phenyl-N-p-Fluorosulfonylbenzoyl Glycinate

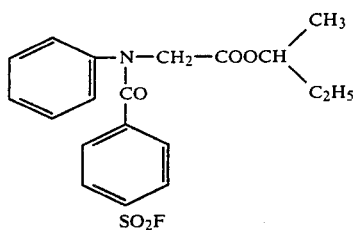

Sec. butyl-N-phenyl glycinate (20.7 g, 0.1 mole) was dissolved in pyridine (50 ml). To it was added p-fluorosulfonylbenzoyl chloride (27 g, 0.12 mole) over a ten minute period. The reaction mixture was stirred for 8 hours and then poured into water. The crude product was collected by filtration and then crystallized from ethanol. 23.8 g (0.06 mole) of the above-identified product was recovered having a melting point of 83° C.

EXAMPLE VI

Allyl-N(p-toluenesulfonyl)-N-Phenyl Glycinate

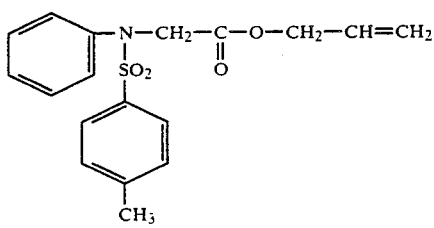

p-Toluenesulfonyl chloride (11.5 g, 0.06 mole) was added over a ten minute period to a solution of allyl-N-phenyl glycinate (9.55 g, 0.05 mole) in pyridine (30 ml). The reaction mixture was stirred at room temperature for 6 hours and then allowed to stand at room temperature overnight.

Pyridine was removed under vacuum and the residue was poured onto water (100 ml). The aqueous mixture was extracted with methylene chloride (3×75 ml). The methylene chloride was washed with water (2×50 ml) and then dried over anhydrous sodium sulfate. Distillation of the methylene chloride left a gummy residue which was crystallized from a mixture of ethanol and water. 12.8 g, (0.037 mole) of the above-identified product was recovered having a melting point of 56° C.

EXAMPLE VII

Methyl-N-(4-chlorobenzenesulfonyl)-N-Phenyl Glycinate

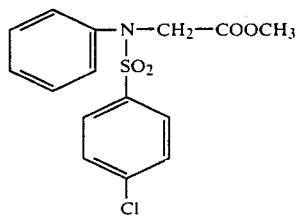

Methyl N-phenyl glycinate (5 g, 0.030 mole) was dissolved in pyridine (20 ml) and 4-chlorobenzene sulfonyl chloride (6.96 g, 0.033 mole) was added to it over a five minute period. The mixture was stirred for 6 hours and pyridine was removed under vacuum. The residue was partitioned between methylene chloride and water. The methylene chloride was dried over magnesium sulfate and evaporated. The residue was crystallized from methanol and water. 2.5 g, (0.0073 mole) of the above-identified product was recovered having a melting point of 103°–104° C.

EXAMPLE VIII

Isobutyl-(N-m-chlorophenylcarbamoyl)-N-Phenyl Glycinate

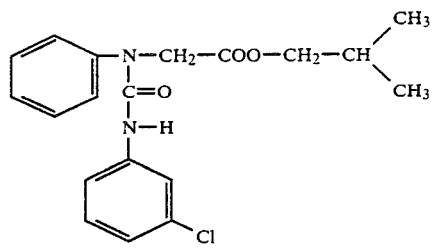

A mixture of isobutyl-N-phenyl glycinate (10.4 g, 0.05 mole) and m-chlorophenylisocyanate (10.71 g, 0.07 mole) was stirred in toluene (20 ml) for 4 hours. Toluene was removed under vacuum and the resulting oil was triturated with hexane. The product was then dissolved in hot cyclohexane and allowed to crystallize. 8 g. (0.02 mole) of the above-identified product was recovered having a melting point of 62° C.

EXAMPLE IX

Ethyl-(N-methylcarbamoyl)-N-Phenyl Glycinate

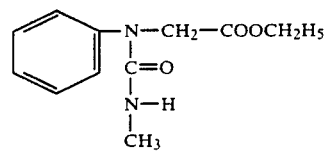

A solution of ethyl-N-phenyl glycinate (8.95 g, 0.05 mole) and methylisocyanate (5.7 g, 0.1 mole) was stirred in toluene (25 ml) at 35° C. for six hours. All the volatiles were removed under vacuum and ethanol (2×30 ml) was added to the residue and evaporated. The residue was crystallized from hexane. 6 g (0.025 mole) of product having a melting point of 69° C. was recovered.

EXAMPLE X

Isobutyl-(N-Methylcarbamoyl)-N-Phenyl Glycinate

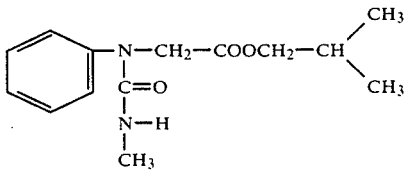

Isobutyl-N-phenyl glycinate (15.52 g, 0.075 mole) was dissolved in chloroform (30 ml). Methylisocyanate (5.7 g, 0.1 mole) was added to it and the solution was stirred at 35° C. for 6 hours. The volatile materials were removed under vacuum, ethanol (2×30 ml) was added to the residue and evaporated. The semisolid product was crystallized from a mixture of methylisobutyl ketone and hexane. 6 g (0.022 mole) of the above-identified product was recovered having a melting point of 57° C.

EXAMPLE XI n-Hexyl-N-Phenyl-N-Phenylcarbamoyl Glycinates

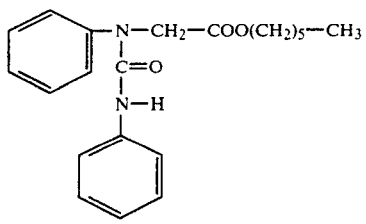

To a solution of n-hexyl-N-phenyl glycinate (23.5 g, 0.1 mole) in toluene (60 ml) was added phenylisocyanate (18 g, 0.15 mole) in toluene (60 ml) was added phenylisocyanate (18 g, 0.15 mole). The reaction solution was heated at 80° C. for 12 hours. Toluene was removed under vacuum and the residue was triturated with petroleum ether. The resulting solid was crystallized from hexane. 19 g, (0.05 mole) of the above-identified product was recovered having a melting point of 58° C.

EXAMPLE XII

Isobutyl-N-Phenyl-N-Cyclohexylcarbamoyl Glycinate

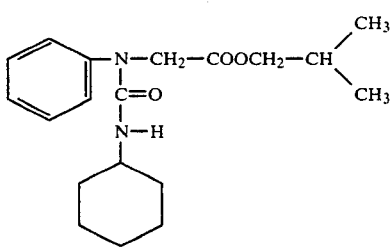

Isobutyl-N-phenyl glycinate (13 g, 0.062 mole) was dissolved in toluene (40 ml), cyclohexylisocyanate (9 g, 0.072 mole) was added to it and the mixture was stirred at 80° C. for 4 hours. Half of the toluene was removed under vacuum and the mixture was allowed to stand overnight. The crude product was separated out, was collected by filtration and crystallized from cyclohexane. 9.8 g, (0.029 mole) of the above-identified product was recovered having a melting point of 81° C.

EXAMPLE XIII

Ethyl-N-Phenyl-N-p-Tolylcarbamoyl Glycinate

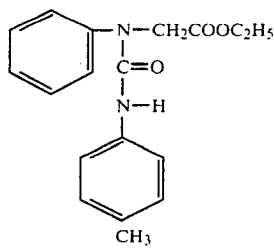

Ethyl N-phenyl glycinate (28 g, 0.15 mole) was dissolved in toluene (50 ml) and p-tolylisocyanate (21 g, 0.17 mole) was added to it. The reaction mixture was stirred at 80° C. for 2 hours and then left at room temperature overnight. The product was collected by filtration and crystallized from carbon tetrachloride to produce 22.46 g (0.07 mole) of the above-identified product having a melting point of 102° C.

EXAMPLE XIV

Ethyl-N-Phenyl-N-p-Chlorophenylcarbamoyl Glycinate

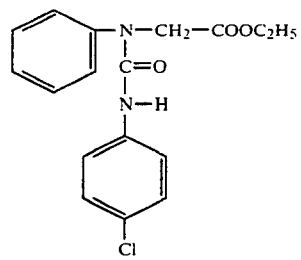

A solution of ethyl-N-phenyl glycinate (26.85 g, 0.15 mole) and p-chlorophenylisocyanate (26 g, 0.17 mole) was heated in toluene (50 ml) at 80° for 5 hours. The reaction mixture was then allowed to stand at room temperature overnight. The product was collected and washed with toluene. After drying it was crystallized from carbon tetrachloride yielding 26 g (0.07 mole) of the above-identified product having a melting point of 107° C.

EXAMPLE XV

Ethyl-N-Phenyl-N-Phenylcarbamoyl Glycinate

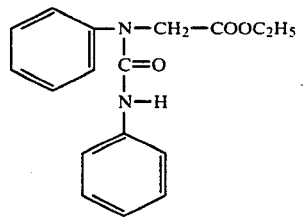

Ethyl-N-phenyl glycinate (26.85 g, 0.15 mole) and phenylisocyanate (20.23 g, 0.17 mole) were heated at 80° for 6 hours in toluene (40 ml). The reaction mixture was allowed to stand at room temperature overnight and the product was filtered, washed with toluene and crystallized from carbon tetrachloride. 20.87 g (0.070 mole) of the above-identified product was recovered having a melting point of 108° C.

EXAMPLE XVI n-Butyl-N-Phenyl-Methylcarbamoyl Glycinate

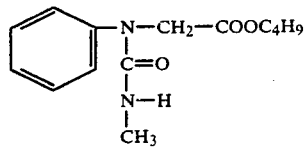

n-Butyl-N-phenyl glycinate (8.28 g, 0.04 mole) was dissolved in toluene (20 ml) and methylisocyanate. (2.85 g, 0.05 mole) was added thereto. The reaction mixture was heated at 40° C. for 23 hours. The volatiles were removed under vacuum and the residue was allowed to stand at room temperature overnight. The residue crystallized from a mixture of carbon tetrachloride and hexane yielding 6.4 g (0.024 mole) of the above-identified product having a melting point of 71° C.

In a similar manner ethyl-N-phenyl glycinate is reacted with methylisothiocyanate to produce ethyl-N-phenyl-N-methylcarbamo-1-thione glycinate of the structure:

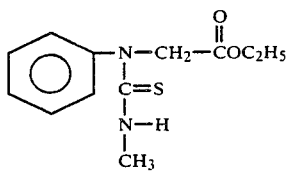

EXAMPLE XVII n-Propyl-N-Phenyl-N-Phenylcarbamoyl Glycinate

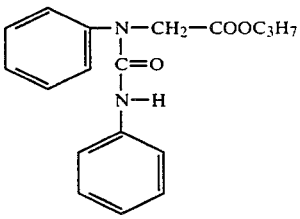

n-Propyl-N-Phenyl glycinate (11.5 g, 0.06 mole) and phenylisocyanate (7.14 g, 0.06 mole) were heated in toluene (30 ml) at 80° C. for 12 hours. On cooling the reaction product crystallized out and was recovered by re-crystallization from a mixture of ethanol and water. 11 g (0.03 mole) of the above-identified product having a melting point of 96° C. was recovered.

In a similar manner n-propyl-N-phenyl glycinate and p-fluorobenzoyl chloride are reacted to produce n-propyl-N-phenyl-(N-p-fluorobenzoyl) glycinate of the structure:

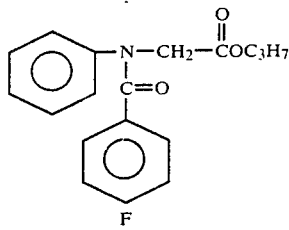

EXAMPLE XVIII

Various compounds prepared by the method presented in the examples were subjected to fungicidal tests to determine relative levels of fungicidal activity. The compounds were applied directly to the fungus in the form of a solution. The activity of the compounds was assessed visually and rated on an activity scale of 0–10 (0=No effect; 10=Very strong fungicidal effect). The compounds were tested for their effect on various fungi, such as bean rust, bean powdery mildew, anthracnose, rhizoctonia and pythium fungi with the results as indicated in Table I.

TABLE I

| Compound | Fungi | Level of Activity |
| --- | --- | --- |
| Isobutyl-N—phenyl | Bean rust | 5 |
| glycinate | Pythium | 5 |
| n-Decyl-N—phenyl | Bean rust | 7 |
| glycinate | Pythium | 6 |
| n-Hexyl-N—phenyl | Bean rust | 5 |
| glycinate | Anthracnose | 3 |
| Isobutyl-N—phenyl-N— cyclohexyl carbamoyl glycinate | Powdery mildew Bean rust | 2 5 |
| Ethyl-N—phenyl-N— p-tolyl carbamoyl glycinate | Powdery mildew Bean rust | 2 1 |
| Ethyl-N—phenyl-N—p- chloro-phenyl carbamoyl glycinate | Powdery mildew Bean rust | 2 1 |
| Ethyl-N—phenyl-N—phenyl- carbamoyl glycinate | Powdery mildew Bean rust Pythium | 4 3 1 |
| n-Butyl-N—phenyl-N— methylcarbamoyl glycinate | Bean rust Anthracnose Pythium | 3 4 10 |
| n-Propyl-N—phenyl-N— phenylcarbamoyl glycinate | Bean rust Anthracnose Pythium | 8 1 5 |
| Allyl-N(p-toluenesul- fonyl)N—phenyl glycinate | Bean rust | 5 |
| Sec-butyl-N—phenyl-N— p-fluoro sulfonyl benzoyl glycinate | Rhizoctonia | 6 |
| Sec.-butyl-N—phenyl glycinate | Rhizoctonia | 6 |
| Ethyl-N—phenyl-N— methylcarbamo-1- thione glycinate | Powdery mildew | 10 |

EXAMPLE XIX

Various novel compounds of the invention were subjected to various pesticidal tests to determine relative levels of pesticidal activity. The compounds were applied directly to pests in the form of a solution—the activity of the compounds were assessed visually and rated on an activity scale of 0–10 (0=no effect; 10=very strong pesticidal effect). The compounds were tested for their effect on various weeds, insects and nematodes with the results as indicated in Table II.

TABLE II

| Compound | Pest | Level of Activity |
|---|---|---|
| n-Propyl-N—phenyl-N—p-fluoro phenyl carbamoyl glycinate | Mexican bean beetle | 7 |
| Ethyl-(N—methyl carbamoyl)N—phenyl glycinate | Morning glory | 6 |
|  | Mustard weed | 8 |
|  | Foxtail millet | 8 |
|  | Crabgrass | 3 |
|  | Pigweed | 4 |
| Methyl-(N—methyl carbamoyl)N—phenyl glycinate | Morning glory | 10 |
|  | Mustard weed | 10 |
|  | Foxtain millet | 2 |
|  | Japanese millet | 2 |
|  | Crabgrass | 5 |
|  | Pigweed | 9 |
| Ethyl-(N—diethyl carbamoyl)-N—phenyl glycinate | Morning glory | 10 |
|  | Mustard weed | 10 |
|  | Foxtail millet | 9 |
|  | Japanese millet | 8 |
|  | Crabgrass | 9 |
|  | Pigweed | 10 |
|  | Rootknot nematode | 10 |
| n-Butyl-(N—diethyl carbamoyl)N—phenyl glycinate | Rootknot nematode | 10 |
| n-Hexyl-N—phenyl-N phenylcarbamoyl glycinate | Mexican bean beetle | 3 |
| Isobutyl-N—phenyl-N cyclohexyl carbamoyl glycinate | Rootknot nematode | 5 |
| Ethyl-N—phenyl-N—p-tolyl carbamoyl glycinate | Rootknot nematode | 3 |
| Ethyl-N—phenyl-N—methylcarbamo-1-thione glycinate | Morning glory | 8 |
|  | Mustard weed | 3 |

TABLE II-continued

| Compound | Pest | Level of Activity |
|---|---|---|
| glycinate | Pigweed | 8 |
| Ethyl-N—phenyl-N—p-chlorophenyl carbamoyl glycinate | Rootknot nematode | 3 |
| n-Butyl-N—phenyl-N methyl carbamoyl glycinate | Morning glory | 8 |
|  | Mustard weed | 4 |
|  | Crabgrass | 6 |
|  | Rootknot nematode | 10 |

I claim:

1. A method of inhibiting the growth of fungi which comprises contacting the fungi with a fungicidal amount of at least one compound of the formula

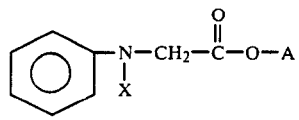

wherein A is hydrogen, or an alkyl group having from 2 to 10 carbon atoms, and X is selected from hydrogen or C=ZNHCH$_3$ wherein Z is oxygen or sulfur.

2. The method of claim 1 wherein the compound is n-butyl-N-phenyl-N-methylcarbamoyl glycinate.

3. The method of claim 1 wherein the compound is n-propyl-N-phenyl-N-methylcarbamoyl glycinate.

4. The method of claim 1 wherein the compound is ethyl-N-phenyl-N-methylcarbamo-1-thione glycinate.

5. The method of claim 1 wherein the compound is isobutyl-N-phenyl glycinate.

6. The method of claim 1 wherein the compound is n-decyl-N-phenyl glycinate.

* * * * *